United States Patent [19]

duMoulin et al.

[11] Patent Number: 5,827,820
[45] Date of Patent: Oct. 27, 1998

[54] AQUEOUS PERITONEAL DIALYSIS SOLUTION

[75] Inventors: Axel duMoulin, Markt-Indersdorf; Jutta Muller-Derlich, München, both of Germany

[73] Assignee: Baxter International Inc., Deerfield, Ill.

[21] Appl. No.: 884,557

[22] Filed: Jun. 27, 1997

Related U.S. Application Data

[63] Continuation of Ser. No. 538,344, Oct. 3, 1995, abandoned, which is a continuation of Ser. No. 150,152, filed as PCT/EP93/00837 Apr. 5, 1993 published as WO93/19792 Oct. 14, 1993, abandoned.

[30] Foreign Application Priority Data

Apr. 6, 1992 [EP] European Pat. Off. ............. 92105911

[51] Int. Cl.⁶ .................. A61K 31/195; A61K 31/70; A61K 38/02; A61M 1/28
[52] U.S. Cl. ................. 514/2; 514/23; 514/561; 604/29
[58] Field of Search ............... 604/29; 210/646, 210/647; 435/1.1, 284.1, 297.1; 514/2, 21, 23, 561; 206/0.5, 219, 221, 524.5

[56] References Cited

U.S. PATENT DOCUMENTS

| | | | |
|---|---|---|---|
| 4,465,488 | 8/1984 | Richmond et al. | 604/414 |
| 4,630,727 | 12/1986 | Feriani et al. | 206/221 |
| 4,959,175 | 9/1990 | Yatzidis | 514/2 |
| 4,997,083 | 3/1991 | Loretti et al. | 206/219 |
| 5,011,826 | 4/1991 | Steudle et al. | 435/1 |
| 5,158,538 | 10/1992 | Shaw | 604/29 |
| 5,211,643 | 5/1993 | Reinhardt et al. | 604/416 |
| 5,296,242 | 3/1994 | Zander | 424/715 |

FOREIGN PATENT DOCUMENTS

| | | |
|---|---|---|
| 36636/89 | 6/1987 | Australia . |
| 0 022 922 | 1/1981 | European Pat. Off. . |
| 0 086 553 | 8/1983 | European Pat. Off. . |
| 0 399 549 | 11/1990 | European Pat. Off. . |
| 0 437 274 | 7/1991 | European Pat. Off. . |
| 0 437 274 B1 | 7/1991 | European Pat. Off. . |
| 87/01 286 | 3/1987 | WIPO . |
| 91/08 008 | 6/1991 | WIPO . |

OTHER PUBLICATIONS

Biasoli et al, "Sodium Lactate and Other Buffers for Peritoneal Dialysis," *Contemporary Dialysis*, pp. 46–49 (1982).
Feriani et al, "Bicarbonate Buffer for CAPD Solution," *Trans Am Soc Artif Intern Organs*, vol. XXXI, pp. 668–672 (1985).
Lindholm et al, "Amino acids for peritoneal dialysis: technical and metabolic implications," *Peritoneal Dialysis*, pp. 149–154 (1986).

*Primary Examiner*—Jeffrey E. Russel
*Attorney, Agent, or Firm*—Thomas S. Borecki; Charles R. Mattenson; Robert M. Barrett

[57] ABSTRACT

The subject matter of this invention concerns an aqueous peritoneal dialysis solution which is obtained immediately prior to administration from two individual solutions, the first of which contains an osmotically active substance and the second of which contains bicarbonate ions, with the first individual solution containing anions of mono- and/or dicarboxylic acids and having a pH value of 4.5–5.8 and with the second individual solution containing an amino acid component or a peptide component and having a pH value of 7.2 to 10.0, and with the ready-to-use solution containing 23 to 26 mmoles/L bicarbonate ions and having a $CO_2$ partial pressure of 25–70 mmHg and a pH value of 7.2 to 7.6

20 Claims, 2 Drawing Sheets

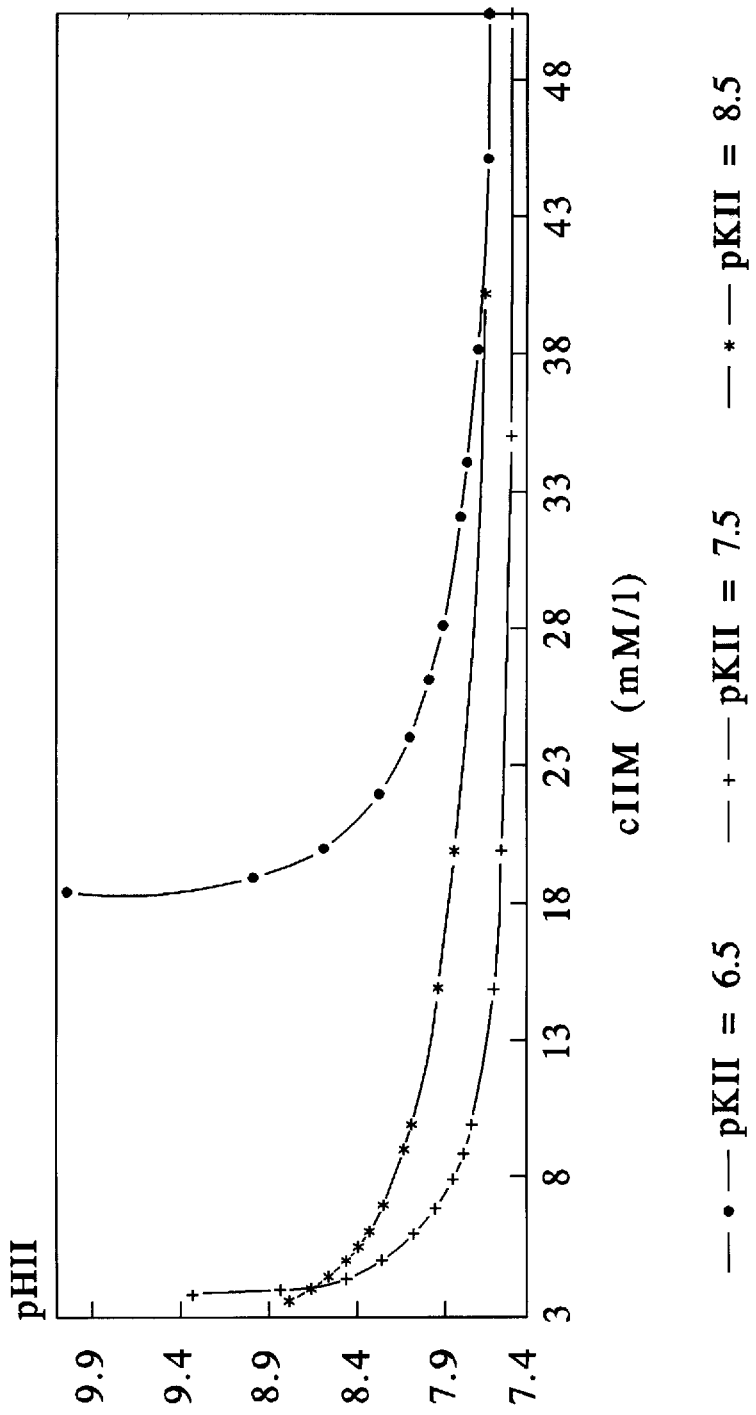

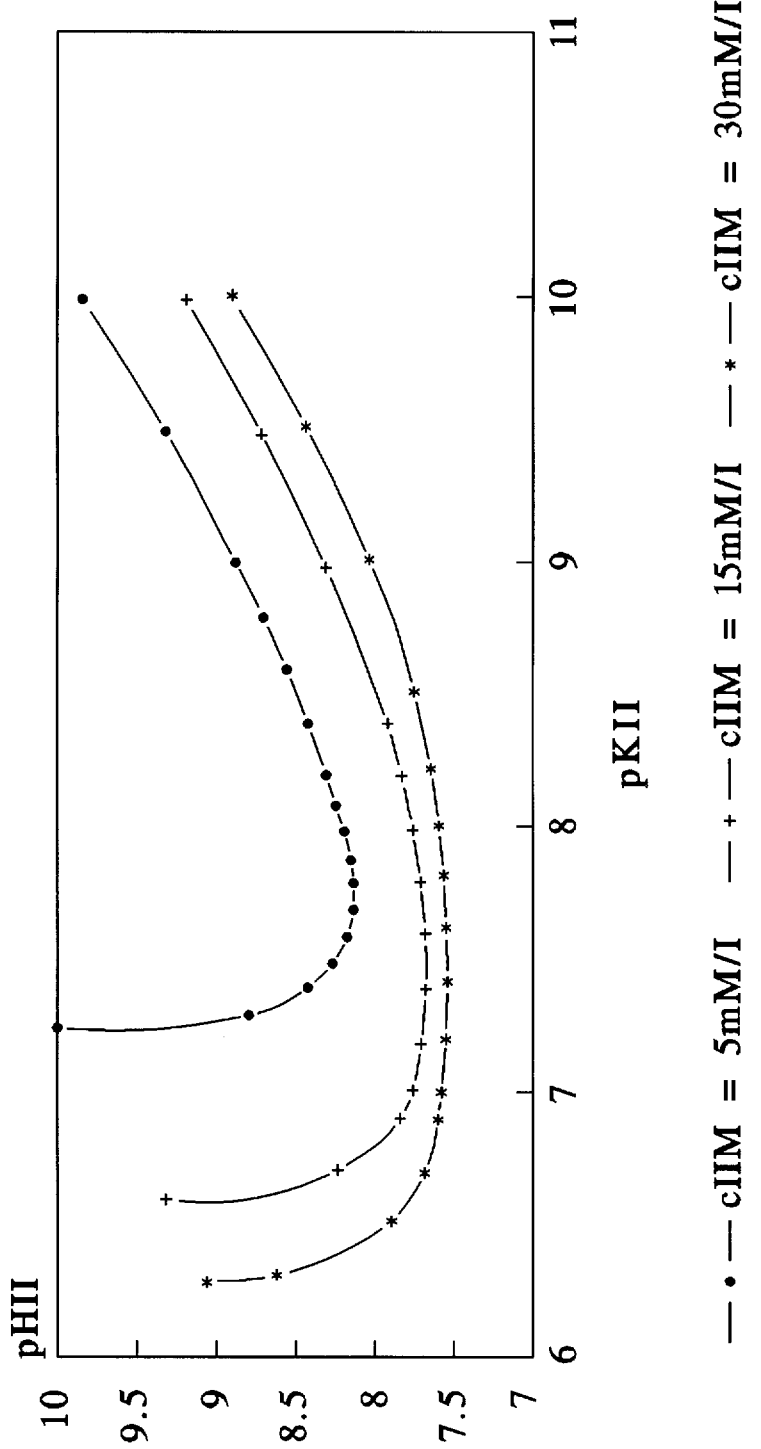

AQUEOUS PERITONEAL DIALYSIS SOLUTION

This application is a continuation of application Ser. No. 08/538,344, filed Oct. 3, 1995, now abandoned, which is a continuation of application Ser. No. 08/150,152, filed Apr. 11, 1994, now abandoned.

The subject matter of this invention concerns an aqueous peritoneal dialysis solution which is obtained immediately prior to application from two individual solutions and which contains an osmotically active substance and bicarbonate ions.

In patients with acute or chronic kidney failure, the limited kidney function has to be compensated for by alternative procedures. Such alternative procedures include hemodialysis and peritoneal dialysis. In the so-called CAPD (continuous ambulatory peritoneal dialysis), the peritoneal cavity of patients suffering from kidney disease is filled several times a day with a fresh peritoneal dialysis solution. With this type of dialysis, detoxification and dehydration takes place by means of the peritoneal membrane which lines the entire abdominal cavity. During the material exchange, the peritoneal membrane acts as a semipermeable membrane through which the dissolved materials pass, such as during diffusion. The details of this material transport are not yet completely understood. Within two to three hours, the concentration of the urinary excreted substances in the freshly administered peritoneal dialysis solution increases due to diffusion. At the same time, fluid is removed by ultrafiltration in correspondence with the osmotic equilibrium. The peritoneal dialysis solutions remains in the abdominal cavity for 4–8 hours and is subsequently withdrawn by means of a catheter. This procedure is generally carried out four times a day and lasts approximately 30–40 minutes. When the peritoneal dialysis solution is replaced, it is necessary to disconnect the extension line between the catheter and the peritoneal dialysis bag.

For reasons of stability, the dialysis solutions so far used especially for continuous ambulatory peritoneal dialysis generally have an acid pH value in a range from 5.2 to 5.5. Such acid dialysis solutions are able to cause damage to the peritoneal membrane, to irritate the defense system of the body, and to lead to pain in the abdominal cavity. This type of acid dialysis and rinsing solution for intraperitoneal administrations has been described, for example, in the German Patent DE-A-3,821,043. However, peritoneal dialysis solutions, the pH value of which is in a range from 7.0 and 7.6, are also available. This type of solution which consists of two individual solutions is known from the European Patent EP-A-0,399,549. One of these individual solutions contains an osmotically active substance and has a pH value of 5.5 to 6.2, and the other individual solution contains bicarbonate ions and has a pH value of 7.0 to 7.6. The problem with this type of peritoneal dialysis solution is that the two individual solutions are not sufficiently stable, particularly as far as the pH value is concerned. In addition, it is very difficult to adjust the pH value of the individual solutions.

Thus, the problem to be solved by this invention was to prepare a peritoneal dialysis solution with a physiological composition relative to the pH value, bicarbonate ion concentration, and $pCO_2$ in which the pH problems mentioned above do not occur.

BRIEF DESCRIPTION OF THE DRAWINGS

FIG. 1 depicts the pH value of the second individual solution (pHII) as a function of the concentration in the peritoneal dialysis solution ($C_{IIM}$) for different pK values of the substances of the second individual solution.

FIG. 2 depicts the pH value of the second individual solution (pHII) as a function of the pK value of the substances of the second individual solution for different concentrations.

The subject matter of this invention is an aqueous peritoneal dialysis solution as described and claimed herein.

In the peritoneal dialysis solution claimed, a physiological composition relative to pH value, bicarbonate ion concentration, and $pCO_2$ is obtained, and the pH value of the individual solutions can be very easily and accurately adjusted due to the buffer effect of the anions of the mono- or dicarboxylic acids or amino acids and peptides.

The pH value of the first individual solution is 4.5 to 5.8, preferably 4.8 to 5.6, but especially 5.0 to 5.5.

The anions of the mono- and/or dicarboxylic acids to be used in the first individual solution include, for example, lactate, acetate, citrate, or formate, preferably lactate or acetate, especially preferred is lactate.

The osmotically active substance to be used in the first individual solution may be, for example, glucose, galactose, polyglucose, or fructose and polyols, such as glycerol or sorbitol. Preferably, glucose or galactose is used, especially preferred is glucose.

The pH value of the second individual solution is 7.2 to 10.0, preferably 7.3 to 8.0, but especially 7.4 to 7.6.

The second individual solution contains mixtures of amino acids or individual amino acids or mixtures of peptides or individual peptides. The selection of the amino acid or the amino acid mixture or the peptide or the peptide mixture is not limited to any particular amino acid or amino acid mixture or to any particular peptide or peptide mixture. Any of the twenty known amino acids can be equally used as the individual component or within a mixture. The peptides used are, for example, hydrolysates from milk proteins.

The pH values of the first and second individual solution are adjusted by means of physiologically compatible acids, such as HCl, lactic acid, or acetic acid, preferably by means of HCl. The two individual solutions are generally mixed at a ratio of 3:1 to 1:3, preferably at a ratio of 1:1 to 1:2.

The following data refer to the composition of the peritoneal dialysis solution, i.e., after the two individual solutions have been combined.

The concentration of the osmotically active substance in the peritoneal dialysis solution is 0.5% to 10%, preferably 0.8% to 7%, especially preferred is 1% to 5%.

The concentration of the anions of the mono- and/or dicarboxylic acids in the peritoneal dialysis solution is 5 to 100 mmoles/L, preferably 10 to 60 mmoles/L, and especially 15 to 40 mmoles/L.

The concentration of the amino acid component or the peptide component in the peritoneal dialysis solution is 0.05 wt % to 2 wt %, preferably 0.1 wt % to 1 wt %, and especially 0.2 wt % to 0.5 wt %.

The concentration of the osmotically active substance is reduced in correspondence with the contribution of the components mentioned above.

Preferably, the peritoneal dialysis solution also contains ions, such as $Na^+$, $Cl^-$, $Ca^{2+}$, $Mg^{2+}$, or $K^+$. The concentrations of these ions are known from prior art, such as mentioned in the European Patents EP-A-0,399,549 or EP-A-0,347,714.

The peritoneal dialysis solution may also contain preferably conventional additives, such as vitamins, hormones which influence the protein metabolism, fatty acids and/or lipids.

According to this invention, the peritoneal dialysis solution has the following parameters: 23–26 mmoles/L bicarbonate ions, $pCO_2$ of 25 to 70 mmHg, pH value 7.2 to 7.6.

The parameters of the peritoneal dialysis solution mentioned above are controlled by means of the two individual solutions, thus making it necessary to accurately adjust the two individual solutions with respect to each other.

The pH value required for the second individual solution, $pH_{II}$, is defined by the equation below, which indicates that the $pH_{II}$ is dependent on the concentrations and the pK values of the substances and on the value of $pH_I$ which is generally predetermined.

$$pH_{11} = pK_{11} + \log\left[\frac{C_{11M}(10^{pH_M - pK_{11}} + 1)}{C_{11M} - D(10^{pH_M - pK_{11}} + 1)} - 1\right] \quad (1)$$

where $$D = C_{1M}\left[\frac{1}{10^{pH_1 - pK_1} + 1} - \frac{1}{10^{pH_M - pK_1} + 1}\right] \quad (2)$$

If only one dissociating substance is present in each of the two individual solutions, the pK value of the carboxyl group can be used for the first individual solution and the pK value of the amino group for the second individual solution.

If two or more dissociating groups are present in the two individual solutions, the compound pK of all dissociating groups is calculated according to the following equation for each of the two individual solutions:

$$pK = \frac{\sum_{i=1}^{i=n} C_i pK_i}{\sum_{i=1}^{i=n} C_i} \quad (3)$$

If, for example, two dissociating groups per substance are present, the $\overline{pK}$ is calculated as follows:

$$\overline{pK} = \frac{pK_1 + pK_2}{2} \quad (4)$$

In this context, it should be noted that in the pH range of $\leq 6.5$, only the anionic groups, and in the pH range of $>6.5$, only the cationic groups are taken into consideration. Thus, for histidine, the pK value of the carboxyl group will not be taken into consideration when calculating the $\overline{pK}$.

The abbreviations have the following meaning:

| | |
|---|---|
| $pH_{II}$ | = pH value of the second individual solution |
| $C_{IIM}$ | = sum of the molar concentrations of bicarbonate ions in the peritoneal dialysis solutions plus the amino acid component or the peptide component from the second individual solution |
| $pK_{II}$ | = pK value of the components of the second individual solution (calculated according to equation (3) if necessary) |
| $pH_M$ | = desired pH value of the peritoneal dialysis solution after combination of the two individual solutions |
| $pH_I$ | = pH value of the first individual solution |
| $C_{IM}$ | = sum of the molar concentrations of the anions of the mono-and/or dicarboxylic acids of the first individual solution in the peritoneal dialysis solution |
| $pK_I$ | = pK value of the carboxylic acids of the first individual solution (calculated according to equation (3) if necessary) |
| $C_i$ | = concentration of substance i |
| $pK_i$ | = pK value of substance i |
| $pK_1$ | = pK value of dissociating group 1 |
| $pK_2$ | = pK value of dissociating group 2 |
| $\overline{pK}$ | = mean pK value for substances with two dissociating groups |

The pH value to which the second individual solution has to be adjusted is calculated by means of equation (1). This requires the calculation of the pK values of both individual solutions, which is done with equation (3). Also, the following parameters must be known or set beforehand: The pH value of the peritoneal dialysis solution (after combination of the two individual solutions); the pH value of the first individual solution which contains the anions of the mono- and/or dicarboxylic acids, and the concentrations of the carboxylic acids or the bicarbonate and the amino acids or the peptides, which are derived from the first or second individual solution respectively, in the peritoneal dialysis solution. With these parameters, (D) in equation (2) is calculated and introduced into equation (1).

By means of the equations above, it is possible to determine the pH value, which is to be set in the second individual solution, for each amino acid or for each amino acid mixture or for each peptide or for each peptide mixture, thus ensuring that the pH value desired in the peritoneal dialysis solution is obtained after the two individual solutions have been combined.

The method used to calculate the pH value of the second individual solution applies analogously to the calculation of the pH value of the first individual solution when the parameters of the second individual solution and that of the peritoneal dialysis solution are known or set respectively.

Since the second individual solution contains bicarbonate, the pH value of the second individual solution may be adjusted in an airtight system to ensure that as little $CO_2$ as possible can escape.

The peritoneal dialysis solution according to this invention can be handled according to well-known procedures, such as described, for example, in the European Patent EP-A-0,161,471. The two individual solutions are preferably sterilized and stored in a bag with two chambers. Prior to the administration of the peritoneal dialysis solution, the two individual solutions can be very easily mixed under sterile conditions simply by opening a valve between the two chambers. Since these bags are generally made of a plastic material, it should be ensured that they are impermeable to gases, especially to $CO_2$. For this reason, the external surface of these bags is sealed with aluminium foil.

As an alternative to sterilizing and mixing the two solutions in a bag with two chambers, it is also possible to sterilize and store the two individual solutions in separate containers (bags, bottles). To mix the two individual solutions as required prior to administration, it is useful to employ a suitable connecting system (tubing system).

For practical reasons, the bicarbonate-containing second individual solution does not contain any $Ca^{2+}$ to avoid a precipitation of $CaCO_3$.

The peritoneal dialysis solution according to this invention is generally used in peritoneal dialysis; however, it can also be used in hemodialysis.

Below, this invention will described in greater detail on the basis of the enclosed drawings:

FIG. (1) shows the pH value to be set in the second individual solution as a function of the concentration in the peritoneal dialysis solution ($C_{IIM}$) and the pK value of the substances from the second individual solution in order to obtain a peritoneal dialysis solution with a pH value of 7.4 after the second individual solution has been mixed with the first individual solution (pH=5.2). The pK value of the first individual solution is $pK_I=4.0$, and the concentration of the mono- and/or dicarboxylic acid anions in the first individual solution is $C_I=70$ mmoles/L.

As FIG. (1) shows, the pH value to be set in the second individual solution is dependent on the concentration of the substances from the second individual solution. At relatively high concentrations and depending on the pK value, the pH value is relatively insensitive to small changes in the concentration. At relatively low concentration, however, small changes in the concentration have a considerable effect on the $pH_{II}$ required. Thus, from the standpoint of the production technology, concentrations in the upper range are definitely preferred.

FIG. (2) shows the pH value in the second individual solution ($pH_{II}$) as a function of the pK value of the substances from the second individual solution and its concentration in the peritoneal dialysis solution to obtain a peritoneal dialysis solution with a pH value of 7.4 after the second individual solution has been combined with the first individual solution ($pH_I=5.2$). The pK value of the first individual solution is $pK_I=4.0$, and the concentration of the mono- and/or dicarboxylic acid anions in the first individual solution is $C_I=70$ mmoles/L.

FIG. (2) clearly shows that, with the exception of the minimum of the curves, two pK values will lead to the same $pH_{II}$. It also shows that, given a set $pK_{II}$ value, the concentration selected determines whether a pH value can be adjusted to ensure that the $pH_M$ value desired can be obtained after the two individual solutions have been mixed.

The following practical example will explain this invention in greater detail.

The peritoneal dialysis solution consists of two individual solutions which are available in two separate compartments of a bag with two chambers. The first individual solution contains glucose, lactate, and electrolytes, and the second individual solution contains bicarbonate ions and 15 different amino acids. Immediately prior to administration, the two individual solutions are combined to obtain a peritoneal dialysis solution. For this mixture, a physiological pH value in the range from 7.20 to 7.60 at 37° C. has been set, whereby the mean pH value attains the physiological pH value of 7.4. The glucose-containing first individual solution was set to have a pH value of 5.00, 5.20, or 5.50 (prior to autoclaving), and based on these data, the pH value for the second individual solution is calculated. Subsequently the second individual solution is adjusted to that pH by means of an acid.

Furthermore, both individual solutions are formulated in such a way that the ready-to-use peritoneal dialysis solution contains 24 mmoles/L of bicarbonate.

First individual solution (glucose/lactate solution)
   2.96%, 5.38%, or 9.63% of glucose
   40 mmoles/L of Na lactate ($pK_s=3.86$)
   4.7 mmoles/L of $CaCl_2$
   2 mmoles/L of $MgCl_2$
   258 mmoles/L of NaCl
Second individual solution (amino acid/bicarbonate solution)
   40.44 mmoles/L of Na bicarbonate ($pK_s=5.98$)
   04. wt % (31.25 mmoles/L) of amino acids
Peritoneal dialysis solution (mixture of the two individual solutions)
   0.75 L of the first individual solution+1.25 L of the second individual solution
   1.11%, 2.02%, or 3.61% of glucose
   0.25 wt % of amino acids
   15 mmoles/L of Na lactate
   24 mmoles/L of Na bicarbonate
   (1.28 mmoles/L of $CO_2$)
   1.75 mmoles/L of $CaCl_2$
   0.75 mmoles/L of $MgCl_2$
   97 mmoles/L of NaCl
Amino acids used:

| | |
|---|---|
| Valine | 2.70 mmoles/L ($pK_a = 9.62$) |
| Leucine | 1.77 mmoles/L ($pK_a = 9.6$) |
| Isoleucine | 1.47 mmoles/L ($pK_a = 9.62$) |
| Methionine | 1.30 mmoles/L ($pK_a = 9.21$) |
| Lysine/HCl | 0.95 mmoles/L ($\overline{pK_a} = 9.74$) |
| Histidine | 1.04 mmoles/L ($\overline{pK_a} = 7.5$) |
| Threonine | 1.24 mmoles/L ($pK_a = 9.12$) |
| Phenylalanine | 0.78 mmoles/L ($pK_a = 9.13$) |
| Tryptophan | 0.30 mmoles/L ($pK_a = 9.39$) |
| Arginine | 1.40 mmoles/L ($\overline{pK_a} = 10.76$) |
| Alanine | 2.42 mmoles/L ($pK_a = 9.69$) |
| Proline | 1.16 mmoles/L ($pK_a = 10.6$) |
| Glycine | 1.54 mmoles/L ($pK_a = 9.6$) |
| Serine | 1.10 mmoles/L ($pK_a = 9.15$) |
| Tyrosine | 0.36 mmoles/L ($pK_a = 9.11$) |

First, the pK values are separately calculated for the first and the second individual solution according to equation (3). Subsequently, by means of equation (2) and the data above, D is calculated for the first individual solution. Since at this stage, all parameters for solving equation (1) are known, the pH value for the second individual solution can now be calculated by means of this equation. The pH value is set with 1 mmol/L of HCl.

The pH values of the first and the second individual solutions were determined prior to autoclaving. After autoclaving, the two solutions are mixed to form a ready-to-use CAPD solution. The number of bags tested per test series was 8 to 9. For all bags duplicate determinations were done. In addition, the $pCO_2$ value in the ready-to-use peritoneal dialysis solution was determined. The results are listed in the table below:

| First individual solution | Second individual solution | CAPD solution after mixing the two individual solutions (37° C.) | | |
|---|---|---|---|---|
| pH (set) | pH (adjusted) | pH (expected) | pH (measured) | $pCO_2$ (mmHg) |
| 5.00 | 7.25 | 7.20 | 7.25 | 62.7 |
| 5.20 | 7.32 | 7.40 | 7.41 | 38.8 |
| 5.50 | 7.57 | 7.60 | 7.59 | 28.1 |

As the table above indicates, the pH values of the peritoneal dialysis solution aimed at are obtained in practice in excellent approximation. For the first value, the variation is only 0.05 pH units and for the two other values, the variation is only 0.01 pH units. However, a prerequisite for the excellent correspondence between the pH value aimed at and the pH value actually obtained in the peritoneal dialysis solution is that the pH values can be accurately adjusted in the individual solutions and that they remain stable.

We claim:

1. A multi-part aqueous peritoneal dialysis solution comprising:
   a first part comprising a first solution, the first solution comprising an osmotically active substance and carboxylic acid anions selected from the group consisting of: monocarboxylic acid anions; dicarboxylic acid anions; and a mixture of monocarboxylic and dicarboxylic anions, the first solution having a pH value of 4.5 to 5.8; and a second part comprising a second solution, the second solution comprising bicarbonate ions and a component selected from the group consisting of: an amino acid component and a peptide component, the second solution having a pH value of 7.2 to 10; the first part and the second part being mixed prior to administration.

2. The solution of claim 1 wherein the two parts are contained in separate chambers of a bag with two chambers.

3. The aqueous peritoneal dialysis solution of claim 1 wherein the second solution contains an amino acid component and the amino acid component is a single amino acid or a mixture of amino acids.

4. The aqueous peritoneal dialysis solution of claim 1 wherein the second solution contains a peptide component and the peptide component is a single peptide or a mixture of peptides.

5. The aqueous peritoneal dialysis solution of claim 1 wherein the osmotically active substance in the first solution is selected from the group consisting of: glucose; galactose; polyglucose; fructose; glycerol; and sorbitol.

6. The aqueous peritoneal dialysis solution of claim 1 wherein the carboxylic acid anion in the first solution is selected from the group consisting of: lactate; acetate; citrate; and formate.

7. The aqueous peritoneal dialysis solution of claim 1 wherein the peritoneal dialysis solution further contains ions in addition to bicarbonate ions.

8. The aqueous peritoneal dialysis solution of claim 7 wherein the ions are $Na^+$, $Cl^-$, $Ca^{2+}$, $Mg^{2+}$, or $K^+$.

9. A method for preparing an aqueous peritoneal dialysis solution comprising the steps of:

providing a first individual solution in a first container, the first individual solution comprising an osmotically active substance, carboxylic acid anions selected from the group consisting of: monocarboxylic acid anions; dicarboxylic acid anions; and a mixture of monocarboxylic and dicarboxylic acid anions, and having a pH value of 4.5 to 5.8;

providing a second individual solution in a second container, the second individual solution comprising bicarbonate ions, a component selected from the group consisting of: amino acid component and peptide component, and having a pH value of 7.2 to 10;

mixing the first individual solution with the second individual solution immediately prior to patient administration in a final container, the dialysis solution containing 23 to 26 mmol/L bicarbonate ions, having a $CO_2$ partial pressure of 27–70 mmHg, and having a pH value of 7.2 to 7.6.

10. The method of claim 9 wherein the second individual solution contains an amino acid component, the amino acid component selected from the group consisting of: a single amino acid; and a mixture of amino acids.

11. The method of claim 9 wherein the osmotically active substance in the first individual solution is selected from the group consisting of: glucose; galactose; polyglucose; fructose; glycerol; and sorbitol.

12. The method of claim 9 wherein the carboxylic acid anion is selected from the group consisting of: lactate; acetate; citrate; and formate.

13. The method of claim 9 further including the step of adding ions selected from the group consisting of: $Na^+$, $Cl^-$, $Ca^{2+}$, $Mg^{2+}$, and $K^+$ to the dialysis solution.

14. The method of claim 9 further comprising mixing the first individual solution with the second individual solution in a ratio of 3:1 to 1:3 by volume.

15. The method of claim 9 wherein the carboxylic acid anions are present in the peritoneal dialysis solution in a concentration of 5 to 100 mmol/L.

16. The method of claim 9 wherein the amino acid component or the peptide component is present in the peritoneal dialysis solution in a concentration of 0.05 wt % to 2 wt %.

17. An apparatus for performing peritoneal dialysis comprising:

a first chamber containing a first solution, the first solution comprising an osmotically active substance and carboxylic anions selected from the group consisting of: monocarboxylic acids; dicarboxylic acids; and mixtures of monocarboxylic and dicarboxylic acids, and having a pH value of 4.5 to 5.8;

a second chamber containing a second solution, the second solution comprising bicarbonate ions and a component selected from the group consisting of: an amino acid component and a peptide component, and having a pH value of 7.2 to 10;

means for combining the first solution and the second solution to form an aqueous peritoneal dialysis solution, the aqueous peritoneal dialysis solution comprising 23 to 26 mmol/L bicarbonate ions, has a $CO_2$ partial pressure of 27–70 mmHg and has a pH value of 7.2 to 7.6.

18. The apparatus of claim 17 wherein the means for combining is a valve between the first chamber and the second chamber which can be opened to mix the first and second solutions together.

19. The apparatus of claim 17 wherein the component in the second chamber is the peptide component.

20. A method for preparing an aqueous peritoneal dialysis solution comprising the steps of:

providing a first individual solution in a first container, the first individual solution comprising an osmotically active substance, carboxylic acid anions selected from the group consisting of: monocarboxylic acid anions; dicarboxylic acid anions; and a mixture of monocarboxylic and dicarboxylic acid anions; and having a pH value of 4.5 to 5.8;

providing a second individual solution in a second container, the second individual solution comprising bicarbonate ions and a peptide component selected from the group consisting of: a single peptide; and a mixture of peptides; and having a pH value of 7.2 to 10;

mixing the first individual solution with the second individual solution immediately prior to patient administration in a final container to form the aqueous peritoneal dialysis solution, the aqueous peritoneal dialysis solution containing 23 to 26 mmol/L bicarbonate ions, having a $CO_2$ partial pressure of 27–70 mmHg, and having a pH value of 7.2 to 7.6.

* * * * *